United States Patent [19]
Wong

[11] Patent Number: 5,807,547
[45] Date of Patent: Sep. 15, 1998

[54] BIOCONTROL OF TAKE-ALL USING PHIALOPHORA SP. (LOBED HYPHOPODIA)

[75] Inventor: Percy Tze Weng Wong, New South Wales, Australia

[73] Assignee: The Minister for Agriculture and Fisheries and the Minister for Mines for the State of New South Wales, Sydney, Australia

[21] Appl. No.: 382,418

[22] Filed: Feb. 2, 1995

[30] Foreign Application Priority Data

Feb. 2, 1994 [AU] Australia ................................. PM3657

[51] Int. Cl.$^6$ .............................. A01N 63/04; C12N 1/14
[52] U.S. Cl. ....................... 424/93.5; 435/254.1; 435/911; 504/117
[58] Field of Search ......................... 424/93.5; 435/254.1, 435/911; 504/117

[56] References Cited

U.S. PATENT DOCUMENTS

| 4,689,398 | 8/1987 | Wu et al. . |
| 5,063,206 | 11/1991 | Bridge et al. . |

FOREIGN PATENT DOCUMENTS

| 38719/93 | 12/1993 | Australia . |
| 278 487 A1 | 5/1990 | Germany . |
| 287 193 A5 | 2/1991 | Germany . |
| 298 038 A5 | 2/1992 | Germany . |
| 36936/89 | 12/1989 | WIPO . |
| WO 92/03056 | 3/1992 | WIPO . |
| 20152/92 | 11/1992 | WIPO . |
| 38953/93 | 10/1993 | WIPO . |
| WO 93/22922 | 11/1993 | WIPO . |

OTHER PUBLICATIONS

ATCC Catalogue of Filamentous Fungi, 18$^{th}$ Ed., 1991, p. 308.
Martyniuk, S. et al., Zbl. Mikrobio., vol. 139(7), pp. 575–579, 1984.
Martyniuk, S., Bulletin OEPP/EPPO Bulletin, vol. 17(4), pp. 609–613, 1987.
Deacon, J.W., Trans. Br. Mycol. Soc., vol. 63(2), pp. 307–327, Oct. 1974.
Holden, J., Trans. Br. Mycol. Soc., vol. 75(1), pp. 97–105, Aug. 1980.
P.T. W. Wong. "Effect of temperature growth of some avirulent fungi . . . " Ann Appl Biol. vol. 95 No. 3, 1980, pp. 291–300.
J.W. Deacon "Biological control of take–all . . . " Biological Abstracts #4516, vol. 64, Phila. USA, pp. 297–308, 1976.
P.T.W. Wong. "Saprophyric survival of gaeumannmyces–graminis . . . "Biological Abstracts #25467, vol. 80, Philadelphia, USA, pp. 455–462, 1984.
P.T.W. Wong et al. "Control of Ophiobolus path in agrostis . . . " Biological Abstracts #19143, Philadelphia, USA, vol. 69, & Ann Appl Biol, vol. 92 No. 2, 1979, pp. 191–198.
P.T.W. Wong et al. "Field control of take–all of wheat . . . " Biological Abstracts #5072, vol. 70, Philadelphia, USA, & Ann Appl Biol. vol. 94, No. 1, 1980, pp. 41–50.
K. Sivasithamparam et al. "Effect of certain isolates . . . " Biological Abstracts #41055, vol. 71, Philadelphia, USA & Aust J. Bot. vol. 28 No. 4, 1980, pp. 421–428.
S. Marttyniuk et al. "Control of the take–all fungus . . . " Biological Abstracts #89591, vol. 79, Philadelphia, USA, & Zentralbl Mikrobiol, vol. 139 No. 7, 1984, pp. 575–579.
C. Augustin. "Possibilities of a diminuition of the pathogenicity . . . " Biological Abstracts #77605, vol. 91, Philadelphia, USA & Zentralbl Mikrobiol, vol. 145 No. 8, 1990, pp. 579–584.
SE 87/00125 (Wettenberg L) 16 Jul. 1988. See abstract.

*Primary Examiner*—Francisco C. Prats
*Attorney, Agent, or Firm*—Nixon & Vanderhye, P.C.

[57] ABSTRACT

A method and composition for the control of take-all disease of winter cereals, especially wheat, barley, triticale and rye and/or take-all patch disease of turfgrasses. The composition comprises at least one isolate of Phialophora sp. which shows cold tolerance as determined by a radial growth rate on a defined quarter-strength potato dextrose agar at 5° C. of at least 1.0 mm/day.

7 Claims, No Drawings

BIOCONTROL OF TAKE-ALL USING PHIALOPHORA SP. (LOBED HYPHOPODIA)

The present invention relates to a method and composition for the control of take-all disease of winter cereals, especially wheat, barley, triticale and rye and/or take-all patch disease of turfgrasses.

Take-all is a root disease of wheat, barley and other small grains caused by the fungus Gaeumannomyces graminis var. tritici. Take-all is a major limitation to cereal cultivation in nearly all cereal growing areas of the world. In Australia alone, yield losses are estimated to exceed $200,000,000 per year. The disease cannot be controlled by resistant cultivars or fungicides. Crop rotation with non-host crops is the main means of control. However, despite crop rotation, yield losses in the second or third cereal crop following the break crop can still be substantial and a better method of control is required.

Biological control of take-all using antagonistic bacteria or fungi has been the subject of study both in Australia and overseas. The take-all fungus, G graminis, includes three varieties with different characteristics. The one that mainly causes take-all in wheat and barley is called G. graminis var. tritici. A second variety causes take-all on oats and is called var. avenae. It can also infect wheat and barley but is much less common than var. tritici. Var. avenae also causes take-all patch disease in turfgrasses. A third variety called var graminis is generally a non-disease causing fungus but has been known to cause a serious disease of rice in the United States of America and the Philippines. This disease is called black sheath rot of rice.

Another fungus, Phialophora sp. (lobed hyphopodia) is closely related to G. graminis var graminis. It has never been recorded as a pathogen of winter cereals, rice and turfgrasses.

It has been suggested in the scientific literature that Phialophora sp. may be useful as a biological control agent for take-all (Wong and Southwell, Ann. appl. Biol. (1980), 94, 41–49; Speakman, Phytopathol. Z. (1984)109, 188–191). Unfortunately, while it has been possible to demonstrate some control, this has typically been only at low levels. For example, Wong and Southwell, Ann. appl Biol. (1980), 94, 41–49, showed that inoculation with Phialophora sp. isolate DAR 32098, gave a statistically significant yield increase over that of uninoculated wheat but this yield was still 54% less than that of healthy wheat. This isolate was later shown to grow on agar at a rate of 0.5 mm/day at 5° C. (see Table 1).

The present inventor has now found that much greater levels of control of take-all can be achieved using Phialophora sp. if the isolate(s) of Phialophora sp. is "cold tolerant". As used herein the term "cold tolerant" is defined as being capable of a radial growth rate at 5° C. at a rate of at least 1.0 mm/day.

Accordingly, in a first aspect the present invention consists in a method of controlling take-all disease in cereals and/or turfgrasses comprising administering to the cereal or turf seed or to the soil a composition comprising at least one isolate of Phialophora sp. and a suitable carrier, the isolate of Phialophora sp. being characterised in that the isolate has a radial growth rate on quarter-strength potato dextrose agar, as hereinafter described, at 5° C. of at least 1.0 mm/day.

In a second aspect the present invention consists in a composition for controlling take-all disease in cereals and/or turfgrasses, the composition comprising an isolate(s) of Phialophora sp. and a carrier, the isolate of Phialophora sp. being characterised in that it is capable of a radial growth rate on quarter-strength potato dextrose agar, as hereinafter described, at 5° C. of at least 1.0 mm/day.

In a preferred embodiment of the present invention the isolate of Phialophora sp. is called KY.

A sample of the isolate of Phialophora sp. KY was deposited under the Budapest Treaty with the Australian Government Analytical Laboratories (AGAL), Pymble, New South Wales, Australia on 31 Jan., 1995. This deposit has been accorded the Accession No N95/6191.

In order that the nature of the present invention may be more clearly understood, preferred forms thereof will now be described with reference to the following examples.

PREPARATION OF QUARTER-STRENGTH POTATO DEXTROSE AGAR (¼ PDA) USED IN GROWTH RATE STUDIES

| Materials | |
| --- | --- |
| Potatoes | 50.0 g |
| Dextrose | 5.0 g |
| (Goodman Fielder Industries, Lidcombe, Australia) | |
| Agar (J-grade) | 15.0 g |
| (Davis Gelatine Co., Botany, Australia) | |
| Distilled Water | 1 liter |

Method

The potatoes were scrubbed free of soil, cut in to quarters or smaller and weighed. The potato pieces were placed in a 1 liter beaker containing 500 ml of distilled water. The agar was added to 500 ml of distilled water in another beaker and stirred. Both beakers were placed in a steamer for 1 hour until all the agar had melted. The contents of the beaker containing the potatoes were filtered through two layers of cheese cloth into a 1 liter measuring cylinder. Hot distilled water was added to the measuring cylinder to make up to 500 ml. This solution was added to the beaker with the melted agar and stirred. The dextrose was then added to this solution and stirred until it was dissolved. The pH of the solution was adjusted to pH 5.8. The solution was then dispersed into 200 ml screw cap bottles and autoclaved at 121° C. for 20 minutes. When cool, the agar was stored at 4° C. and used within 2 weeks of storage. Agar plates were prepared by melting the agar in the bottles and dispensing 15 ml aliquots into 9 cm diameter sterile plastic petri plates. The surface of the solidified agar was dried for 5 minutes in a laminar flow cabinet. Colonies of the test fungi were grown on the agar for 4 days at 20° C. Five mm plugs from the growing margins of the colonies were made with a sterile cork borer. An agar plug was then placed at the centre of each agar plate. There were 3 replicate plates per fungus at each temperature of incubation. At the higher temperatures (15° C., 20° C. and 25° C.) the radii of the fungal colonies were measured daily. For the lower temperatures (5° and 1° C.), measurements were made after 5 days and every 2–3 days thereafter.

Screening for Candidate Fungi

Isolates of Phialophora sp. were obtained by plating out root pieces of grass species collected from wheat growing areas in New South Wales. The roots were washed free of soil and 3–4 cm pieces of roots were surface-sterilised for 30–60 seconds in 10% hypochlorite in 50% ethanol. The roots were rinsed with sterile water and cut into 1 cm pieces aseptically. These root pieces were then plated on agar medium and incubated at 10° C. After seven days, fungi resembling Phialophora sp. were cut out and replated on the same medium. Pure cultures were obtained and identified according to Walker (Chapter 2 in Biology and Control of Take-all, eds. Asher M. J. C. and Shipton P. J., Academic Press, 1981). They were then tested for their growth rates at 5° C., 10° C., 15° C., 20° C. and 25° C. The fastest growing isolates at 5° C. were then tested in a field experiment for their ability to suppress take-all disease.

Field Experiment 1

Inocula of the take-all fungus and Phialophora sp. (lobed hyphopodia) were prepared by growing each fungus on moistened oat grains that had been sterilized (60 minutes at 121° C.) for two successive days. After four weeks, the colonized oat grains were air-dried at room temperature for seven days and stored at 4° C. until ready for use.

The field experiment was carried out at the Agricultural Research Station at Cowra, New South Wales.

The treatments were:
(i) No inoculation (healthy control)
(ii) Take-all alone
(iii) Take-all and Phialophora sp.

The wheat seed was mixed with the fungal inoculum or inocula and sown into the same furrow, The plots were 1.5 m wide by 12.5 m long. The field experiment was laid out as a randomised complete block design with six replications. Wheat seed, the take-all inoculum and Phialophora sp. inoculum were mixed in a 2:2:1 ratio respectively and sown at the rate of 60 kg of wheat per hectare. The plots were assessed for take-all disease on a 0–10 scale, where 10 =maximum disease, and colonisation of the roots by Phialophora sp. (lobed hyphopodia). Grain yields were obtained at crop maturity.

Field Experiment 2

Inocula of the take-all fungus and three isolates of Phialophora sp. (lobed hyphopodia) were prepared as in Experiment 1. The field experiment was carried out at the Biological and Chemical Research Institute, Rydalmere.

The treatments were:
(i) No inoculation (Healthy control)
(ii) Take-all alone
(iii) Take-all+Phialophora sp. (K1)
(iv) Take-all+Phialophora sp.(KC)
(v) Take-all+Phialophora sp. (6A).

The wheat seed was mixed with the fungal inoculum or inocula and sown in the same furrow. The plots were single rows 1.5 m long. The experiment was set out as a randomised complete block design with four replications. Wheat was sown at the rate of 1.5 g/plot and each fungal inoculum was used at the rate of 1.5 g/plot. The plots were assessed for take-all disease on a 0–5 scale, where 5+maximum disease. Grain yields were obtained at crop maturity.

Results

1. Screening for Candidate Fungi

Growth rate studies at temperatures of 5°–25° C. showed that Phialophora sp. isolates KY, K1 and KC grew at 5° C. at the rate of 1.4, 1.2 and 1.0 mm/day respectively (Table 1).

Phialophora sp. isolates DAR 32098 grew at 0.5 mm/day while isolate 6A did not grow at 5° C. on the defined media. Isolates of pathogenic G. graminis var. tritici tested either did not grow or grew at a slower rate (e.g. 921) on these plates at 5° C. (Table 1).

2. Field Experiment 1

There was significantly more disease in the take-all alone plots than in the take-all plus Phialophora sp. plots (Table 2). The mean grain yield of the plots protected with Phialophora sp. was significantly greater ($P<0.05$) than that of the take-all alone plots but was not significantly different to the mean yield of the healthy uninoculated plots (Table 2). Phialophora sp. was re-isolated from roots of wheat plants in plots inoculated with the fungus.

3. Field Experiment 2

Plots inoculated with Phialophora sp. (isolates K1 and KC) had significantly ($P \leq 0.05$) less take-all disease and yielded significantly ($P \leq 0.05$) more than the take-all alone treatment (Table 3). These isolates are capable of growing at 5° C. on the hereinbefore described ¼ PDA at a rate of 1.0 m/day or greater (Table 1). In contrast, Phialophora sp. (isolate 6A) which does not grow at 5° C. (Table 1) did not protect wheat against take-all and produced yields not significantly ($P \leq 0.05$) different to that of the take-all alone treatment (Table 3).

These results demonstrate that cold tolerance is an important characteristic for the Phialophora sp. to be effective against take-all.

The importance of cold tolerance for effective biocontrol may be deduced from the results shown in Tables 3 and 4. In Table 3, two cold tolerant Phialophora sp. isolates, K1 and KC, gave significantly better control than isolate 6A, which does not grow at 5° C. In fact, isolate 6A did not protect against take-all in this experiment.

A second line of evidence is shown in Table 4. Data from a paper by Wong and Southwell (1980) showed that Phialophora sp. (isolate DAR 32098), which grows on agar at the rate of 0.5 mm/day at 5° C., protected wheat against take-all to some degree but its grain yield was less than half (45.7%) of that of healthy wheat. In contrast, Phialophora sp. (isolate KY), which grows at the rate of 1.4 mm/day on agar at 5° C., gave a higher level of protection and its grain yield was 93.1% of that of healthy wheat. This compares favourably with the relative yields of 93.7% and 87.6% for the other two cold tolerant Phialophora sp. isolates, K1 and KC, respectively (Table 3).

From Table 5, it may be seen that the growth rate of Phialophora sp. isolate KY may vary to some degree depending on the source of agar medium used. Accordingly, the criterion of cold tolerance as used herein of radial growth rate on ¼ PDA of at least 1.0 mm/day is to be assessed using ¼ PDA prepared according to the protocol set out above.

TABLE 1

Radial growth rate (mm/day) of isolates of Phialophora sp. and *G.g. tritici* (921) at various temperatures on quarter strength potato dextrose agar.

| FUNGUS | TEMPERATURES | | | | |
|---|---|---|---|---|---|
| | 5° C. | 10° C. | 15° C. | 20° C. | 25° C. |
| Phialophora sp. (KY) | 1.4 ± 0.2 | 2.8 ± 0.1 | 3.8 ± 0.1 | 5.5 ± 0.2 | 6.0 ± 0.5 |
| Phialophora sp. (K1) | 1.2 ± 0.2 | 2.3 ± 0.1 | 3.6 ± 0.1 | 2.4 ± 0.2 | 2.2 ± 0.2 |
| Phialophora sp. (KC) | 1.0 ± 0.2 | 1.7 ± 0.2 | 3.9 ± 0.3 | 6.5 ± 0.2 | 4.1 ± 0.3 |
| Phialophora sp. (DAR 32098) | 0.5 ± 0.2 | 2.4 ± 0.2 | 4.7 ± 0.3 | 6.3 ± 0.2 | 6.5 ± 0.4 |

TABLE 1-continued

Radial growth rate (mm/day) of isolates of Phialophora sp.
and G.g. tritici (921) at various temperatures on quarter
strength potato dextrose agar.

| FUNGUS | TEMPERATURES | | | | |
|---|---|---|---|---|---|
| | 5° C. | 10° C. | 15° C. | 20° C. | 25° C. |
| Phialophora sp. (6A) | 0.0 | 1.8 ± 0.1 | 4.0 ± 0.2 | 5.7 ± 0.3 | 6.4 ± 0.3 |
| G.g. tritici (921) | 0.5 ± 0.1 | 1.6 ± 0.1 | 3.6 ± 0.2 | 4.7 ± 0.2 | 4.6 ± 0.3 |

TABLE 2

Biocontrol of take-all using Phialophora sp. (lobed
hyphopodia) isolate KY in a field experiment.

| TREATMENT | DISEASE RATING (0–10) | GRAIN YIELD (kg/plot) |
|---|---|---|
| Healthy Control | 0.0 | 7.2 |
| Take-all alone | 5.8 | 4.7 |
| Take-all + Phialophora sp. | 2.4 | 6.7 |
| Lsd (P = 0.05) | 1.2 | 0.9 |

TABLE 3

Biocontrol of take-all using different isolates of
Phialophora sp. (lobed hyphopodia).

| Treatment | Disease Rating (0–5) | Grain Yield (g/plot) | Grain Yield as % of healthy wheat |
|---|---|---|---|
| Nil | 0 | 118.2 | 100.0 |
| Take-all alone | 4.2 | 76.3 | 64.6 |
| Take-all + Phialophora sp. (K1) | 2.3 | 110.7 | 93.7 |
| Take-all + Phialophora sp. (KC) | 2.6 | 103.5 | 87.6 |
| Take-all + Phialophora sp. (6A) | 4.0 | 80.6 | 68.2 |
| Lsd (P = 0.05) | 1.2 | 17.1 | — |

TABLE 4

Relative efficacy of two isolates of Phialophora sp.
(lobed hyphopodia) in controlling take-all.

| Phialophora sp. isolate | Growth Rate at 5° C. (mm/day) | Grain Yield of Inoculated Treatment (kg/plot) | Grain Yield of Healthy Wheat (kg/plot) | Grain Yield of Inoculated as % of Healthy Wheat |
|---|---|---|---|---|
| DAR 32098* | 0.5 ± 0.2 | 2.03 | 4.44 | 45.7 |
| KY** | 1.4 ± 0.2 | 6.7 | 7.2 | 93.1 |

*Data from Wong and Southwell (1980), p45, Table 4.
**Data from Tables 1 and 2, this document.

TABLE 5

Effect of media on the growth rates (mm/day) of
Phialophora sp. (lobed hyphopodia) isolate KY at various temperatures.

| Medium | Temperatures | | | | |
|---|---|---|---|---|---|
| | 5° C. | 10° C. | 15° C. | 20° C. | 25° C. |
| ¼PDA (laboratory made) | 1.4 ± 0.2 | 2.8 ± 0.1 | 3.8 ± 0.1 | 5.5 ± 0.2 | 6.0 ± 0.5 |
| ¼PDA (Oxoid) | 0.9 ± 0.2 | 2.2 ± 0.1 | 4.9 ± 0.2 | 6.1 ± 0.4 | 7.0 ± 0.8 |
| Czapek-Dox (Oxoid) + 0.2 g/L Yeast Extract (Difco) | 1.0 ± 0.2 | 2.7 ± 0.1 | 5.2 ± 0.3 | 7.3 ± 0.4 | 8.2 ± 0.6 |

As is clear from the above results the present inventor has discovered a biological method and composition for control of take-all disease of winter cereals.

The method and composition of the present invention achieved a significant reduction in disease in field experiments employing wheat seeds mixed with the biocontrol fungus.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

I claim:

1. A method of controlling take-all disease in at least one of cereals and turfgrasses comprising administering to cereal, turf seed or soil a composition comprising at least one isolate of Phialophora sp. (lobed hyphopodia) and a carrier, the at least one isolate of Phialophora sp. (lobed hyphopodia) having a radial growth rate on quarter-strength potato dextrose agar at 5° C. of at least 1.0 mm/day.

2. The method as claimed in claim 1 in which the at least one isolate of Phialophora sp. (lobed hyphopodia) has a radial growth rate on quarter-strength potato dextrose agar at 5° C. of at least 1.4 mm/day.

3. The method as claimed in claim 1 in which the at least one isolate of Phialophora sp. is KY (N95/6191).

4. A composition for controlling take-all diseases in at least one of cereals and turfgrasses, the composition comprising at least one isolate of Phialophora sp. (lobed hyphopodia) and a carrier, the at least one isolate of Phialophora sp. (lobed hyphopodia) having a radial growth rate on quarter-strength potato dextrose agar at 5° C. of at least 1.0 mm/day.

5. The composition as claimed in claim 4 in which the at least one isolate of Phialophora sp. (lobed hyphopodia) has a radial growth rate on quarter-strength potato dextrose agar at 5° C. of at least 1.4 mm/day.

6. The composition as claimed in claim 4 in which the at least one isolate of Phialophora sp. is KY (N95/6191).

7. A biologically pure culture of Phialophora sp. KY (N95/6191).

* * * * *